(12) United States Patent
Faries, Jr. et al.

(10) Patent No.: US 9,119,912 B2
(45) Date of Patent: Sep. 1, 2015

(54) METHOD AND APPARATUS FOR CONTROLLING PRESSURIZED INFUSION AND TEMPERATURE OF INFUSED LIQUIDS

(75) Inventors: Durward I. Faries, Jr., Las Vegas, NV (US); Bruce R. Heymann, Vienna, VA (US); Calvin Blankenship, Frostburg, MD (US); David Hendrix, Ashburn, VA (US)

(73) Assignee: Medical Solutions, Inc., Chantilly, VA (US)

(*) Notice: Subject to any disclaimer, the term of this patent is extended or adjusted under 35 U.S.C. 154(b) by 2174 days.

(21) Appl. No.: 11/439,426

(22) Filed: May 24, 2006

(65) Prior Publication Data

US 2006/0253075 A1 Nov. 9, 2006

Related U.S. Application Data

(62) Division of application No. 10/095,100, filed on Mar. 12, 2002, now Pat. No. 7,238,171.

(60) Provisional application No. 60/275,256, filed on Mar. 12, 2001.

(51) Int. Cl.
*A61M 5/148* (2006.01)
*A61M 5/44* (2006.01)

(52) U.S. Cl.
CPC ............. *A61M 5/1483* (2013.01); *A61M 5/445* (2013.01)

(58) Field of Classification Search
USPC ............... 604/500, 19, 20, 21, 503, 506, 507, 604/508, 505, 113, 114, 118, 141, 142, 246, 604/251, 253; 607/96, 104, 105, 113, 114; 128/DIG. 12, DIG. 13
See application file for complete search history.

(56) References Cited

U.S. PATENT DOCUMENTS 522,866 A 7/1894 Weinhagen et al.
558,979 A 4/1896 Noble (Continued)

FOREIGN PATENT DOCUMENTS

CA 2103791 10/1993
DE 37 42 927 7/1989

(Continued)

OTHER PUBLICATIONS

Cahill, New Name, New Helmsman, JEMS, Aug. 1996.

(Continued)

*Primary Examiner* — Manuel A Mendez
(74) *Attorney, Agent, or Firm* — Edell, Shapiro & Finnan, LLC (57) ABSTRACT

A system for controlling pressurized infusion and temperature of intravenous fluids according to the present invention includes a housing, a heating assembly and a flexible cover. The heating assembly is recessed within the housing and includes a generally U-shaped configuration to surround and uniformly heat fluid within a fluid container placed thereon. The cover wraps around a portion of the fluid container to secure the fluid container against the heating assembly. The cover includes a pressurization member to apply a desired pressure to the fluid container to achieve a desired flow rate of intravenous fluid from the fluid container to an infusion site on a patient. The system further includes a controller to control the heating assembly and pressure within the pressurization member in accordance with desired temperature and pressure information entered into the controller for system operation.

27 Claims, 3 Drawing Sheets

(56) References Cited

U.S. PATENT DOCUMENTS

| | | |
|---|---|---|
| 675,647 A | 6/1901 | Andersen et al. |
| 785,524 A | 3/1905 | Shea |
| 803,352 A | 10/1905 | Meyer |
| 1,062,111 A | 5/1913 | Nylander |
| 1,092,643 A | 4/1914 | Goolsby |
| 1,110,919 A | 9/1914 | Gamble |
| 1,223,274 A | 4/1917 | Hallock |
| 1,390,500 A | 9/1921 | Christian |
| 1,479,451 A | 1/1924 | Buckstein |
| 1,493,450 A | 5/1924 | Richardson |
| 1,659,719 A | 2/1928 | Blake |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |
| 1,847,573 A | 3/1932 | Rupp |
| 1,847,954 A | 3/1932 | Fisher |
| 1,960,417 A | 5/1934 | Pain, Jr. |
| 1,982,213 A | 11/1934 | Hopkins |
| 1,987,119 A | 1/1935 | Long |
| 1,995,302 A | 1/1935 | Goldstein |
| 2,006,902 A | 12/1936 | Beasley |
| 2,087,586 A | 7/1937 | Tishman |
| 2,124,293 A | 7/1938 | Goldstein |
| 2,175,099 A | 10/1939 | Abbott |
| 2,204,764 A | 6/1940 | Mayo |
| 2,214,215 A | 9/1940 | Watermann et al. |
| 2,254,994 A | 9/1941 | Butland |
| 2,357,692 A | 9/1944 | Saffady |
| 2,470,481 A | 5/1949 | Freeman |
| 2,576,874 A | 11/1951 | Acton |
| 2,701,789 A | 2/1955 | White |
| 2,713,112 A | 7/1955 | Mills et al. |
| 2,741,099 A | 4/1956 | Beane |
| 2,766,907 A | 7/1956 | Mills et al. |
| 2,841,132 A | 7/1958 | Phillip |
| 2,880,764 A | 4/1959 | Pelavin |
| 2,885,526 A | 5/1959 | Paulding |
| 2,910,981 A | 11/1959 | Wilson et al. |
| 2,990,875 A | 7/1961 | Samuels et al. |
| 2,994,760 A | 8/1961 | Pecoraro et al. |
| 3,051,582 A | 8/1962 | Muckler et al. |
| 3,140,716 A | 7/1964 | Harrison et al. |
| 3,157,727 A | 11/1964 | Hardy et al. |
| 3,193,339 A | 7/1965 | Cooper |
| 3,241,603 A | 3/1966 | Nagata |
| 3,247,851 A | 4/1966 | Seibert |
| 3,255,812 A | 6/1966 | Bayane et al. |
| 3,293,868 A | 12/1966 | Gonzalez |
| 3,329,202 A | 7/1967 | Birman |
| 3,353,589 A | 11/1967 | Tope et al. |
| 3,370,153 A | 2/1968 | Du Fresne et al. |
| 3,386,498 A | 6/1968 | Funfstuck |
| 3,475,590 A | 10/1969 | Pins |
| 3,485,245 A | 12/1969 | Lahr et al. |
| 3,500,366 A | 3/1970 | Chesney et al. |
| 3,536,132 A | 10/1970 | Pecoraco et al. |
| 3,551,641 A | 12/1970 | Truhan |
| 3,563,090 A | 2/1971 | Deltour |
| 3,590,215 A | 6/1971 | Anderson et al. |
| 3,591,290 A | 7/1971 | Zinner et al. |
| 3,596,515 A | 8/1971 | Cramer |
| 3,612,059 A | 10/1971 | Ersek |
| 3,612,165 A | 10/1971 | Haynes |
| 3,614,385 A | 10/1971 | Horstmann |
| 3,629,552 A | 12/1971 | Edging |
| 3,640,277 A | 2/1972 | Adelberg |
| 3,651,695 A | 3/1972 | Brown |
| 3,704,625 A | 12/1972 | Seto et al. |
| 3,713,302 A | 1/1973 | Reviel |
| 3,777,187 A | 12/1973 | Kohn |
| 3,801,278 A | 4/1974 | Wagner et al. |
| 3,826,305 A | 7/1974 | Fishman |
| 3,858,106 A | 12/1974 | Launius |
| 3,861,213 A | 1/1975 | Parker |
| 3,864,976 A | 2/1975 | Parker |
| 3,879,171 A | 4/1975 | Tulis |
| 3,895,741 A | 7/1975 | Nugent |
| 3,908,652 A | 9/1975 | Weissinger |
| 3,940,742 A | 2/1976 | Hudspeth et al. |
| 4,024,377 A | 5/1977 | Henke |
| 4,038,519 A | 7/1977 | Foucras |
| 4,063,551 A | 12/1977 | Sweeney |
| 4,084,080 A | 4/1978 | McMahan |
| 4,090,514 A | 5/1978 | Hinck et al. |
| 4,098,123 A | 7/1978 | Granzow, Jr. |
| 4,167,663 A | 9/1979 | Granzow, Jr. et al. |
| 4,189,995 A | 2/1980 | Lohr et al. |
| 4,233,495 A | 11/1980 | Scoville et al. |
| 4,293,762 A | 10/1981 | Ogawa |
| 4,309,592 A | 1/1982 | Le Boeuf |
| 4,314,484 A | 2/1982 | Bowman |
| 4,318,276 A | 3/1982 | Salo et al. |
| 4,328,676 A | 5/1982 | Reed |
| 4,331,859 A | 5/1982 | Thomas et al. |
| 4,336,435 A | 6/1982 | Kashyap et al. |
| 4,356,383 A | 10/1982 | Dahlberg |
| 4,364,234 A | 12/1982 | Reed |
| 4,375,813 A | 3/1983 | Hessel |
| 4,384,578 A | 5/1983 | Winkler |
| 4,397,648 A | 8/1983 | Knute |
| 4,407,133 A | 10/1983 | Edmonson |
| 4,408,905 A | 10/1983 | Ehrenkranz |
| 4,419,568 A | 12/1983 | Vanoverloop |
| 4,430,077 A | 2/1984 | Mittleman et al. |
| 4,430,078 A | 2/1984 | Sprague |
| 4,432,761 A | 2/1984 | Dawe |
| 4,448,204 A | 5/1984 | Lichtenstein |
| 4,455,478 A | 6/1984 | Guibert |
| 4,464,563 A | 8/1984 | Jewett |
| 4,468,137 A | 8/1984 | Hilsum et al. |
| 4,476,877 A | 10/1984 | Barker |
| 4,481,410 A | 11/1984 | Bortnik |
| 4,490,884 A | 1/1985 | Vickers |
| 4,495,402 A | 1/1985 | Burdick et al. |
| 4,498,901 A | 2/1985 | Finch |
| 4,509,532 A | 4/1985 | DeVries |
| 4,509,943 A | 4/1985 | Hanzawa |
| 4,522,308 A | 6/1985 | Sullivan |
| 4,523,078 A | 6/1985 | Lehmann |
| 4,529,309 A | 7/1985 | Pettersson et al. |
| 4,531,941 A | 7/1985 | Zasuwa |
| 4,532,414 A | 7/1985 | Shah et al. |
| 4,533,350 A | 8/1985 | Danby et al. |
| 4,551,136 A | 11/1985 | Mandl |
| 4,552,277 A | 11/1985 | Richardson et al. |
| 4,572,536 A | 2/1986 | Doughty |
| 4,585,441 A | 4/1986 | Archibald |
| 4,586,691 A | 5/1986 | Kozlow |
| 4,605,840 A | 8/1986 | Koopman |
| 4,613,327 A | 9/1986 | Tegrarian et al. |
| 4,614,514 A | 9/1986 | Carr et al. |
| 4,625,086 A | 11/1986 | Karino |
| 4,626,243 A | 12/1986 | Singh et al. |
| 4,628,186 A | 12/1986 | Bergemann et al. |
| 4,634,432 A | 1/1987 | Kocak |
| 4,647,756 A | 3/1987 | Willis |
| 4,651,813 A | 3/1987 | Witt et al. |
| 4,657,004 A | 4/1987 | Coffey |
| 4,673,820 A | 6/1987 | Kamen |
| 4,674,977 A | 6/1987 | Hoselton |
| 4,678,460 A | 7/1987 | Rosner |
| 4,680,445 A | 7/1987 | Ogawa |
| 4,680,977 A | 7/1987 | Conero et al. |
| 4,682,979 A | 7/1987 | Girouard |
| 4,684,367 A | 8/1987 | Schaffer et al. |
| 4,705,505 A | 11/1987 | Fried |
| 4,707,587 A | 11/1987 | Greenblatt |
| 4,709,135 A | 11/1987 | Dietrich et al. |
| 4,718,896 A | 1/1988 | Arndt et al. |
| 4,726,193 A | 2/1988 | Burke et al. |
| 4,735,609 A | 4/1988 | Comeau et al. |
| 4,745,248 A | 5/1988 | Hayes |
| 4,747,450 A | 5/1988 | Ikegame et al. |

(56) References Cited

U.S. PATENT DOCUMENTS

| | | |
|---|---|---|
| 4,747,826 A | 5/1988 | Sassano |
| 4,756,299 A | 7/1988 | Podella |
| 4,759,749 A | 7/1988 | Verkaart |
| 4,772,778 A | 9/1988 | Ogawa |
| 4,781,548 A | 11/1988 | Alderson et al. |
| 4,782,212 A | 11/1988 | Bakke |
| 4,801,777 A | 1/1989 | Auerbach |
| 4,804,367 A | 2/1989 | Smith et al. |
| 4,808,159 A | 2/1989 | Wilson |
| 4,823,554 A | 4/1989 | Trachlenberg et al. |
| 4,823,833 A | 4/1989 | Hogan et al. |
| 4,832,689 A | 5/1989 | Mauerer et al. |
| 4,844,074 A | 7/1989 | Kurucz |
| 4,844,397 A | 7/1989 | Skakoon et al. |
| 4,847,470 A | 7/1989 | Bakke |
| 4,859,360 A | 8/1989 | Suzuki et al. |
| 4,874,033 A | 10/1989 | Chatelain et al. |
| 4,874,359 A | 10/1989 | White et al. |
| 4,878,537 A | 11/1989 | Verkaart |
| 4,878,588 A | 11/1989 | Ephraim |
| 4,883,117 A | 11/1989 | Dobbs et al. |
| 4,894,207 A | 1/1990 | Archer et al. |
| 4,900,308 A | 2/1990 | Verkaart |
| 4,904,848 A | 2/1990 | Colevas |
| 4,906,816 A | 3/1990 | Van Leerdam |
| 4,910,386 A | 3/1990 | Johnson |
| 4,916,386 A | 4/1990 | Schulz |
| 4,923,681 A | 5/1990 | Cox et al. |
| 4,934,152 A | 6/1990 | Templeton |
| 4,934,336 A | 6/1990 | White |
| 4,935,604 A | 6/1990 | Allen et al. |
| 4,936,828 A | 6/1990 | Chiang |
| 4,961,320 A | 10/1990 | Gutmann |
| 4,991,976 A | 2/1991 | Byles |
| 4,994,021 A | 2/1991 | Smith et al. |
| 5,000,581 A | 3/1991 | Yata et al. |
| 5,013,889 A | 5/1991 | Bakke |
| 5,019,047 A | 5/1991 | Kriesel |
| 5,040,380 A | 8/1991 | Gregory |
| 5,042,455 A | 8/1991 | Yue et al. |
| 5,059,182 A | 10/1991 | Laing |
| 5,061,241 A | 10/1991 | Stephens, Jr. et al. |
| 5,061,630 A | 10/1991 | Knopf et al. |
| 5,063,994 A | 11/1991 | Verkaart |
| 5,073,167 A | 12/1991 | Carr et al. |
| 5,074,658 A | 12/1991 | Tavlarides et al. |
| 5,075,167 A | 12/1991 | Yamauchi et al. |
| 5,081,697 A | 1/1992 | Manella |
| 5,096,078 A | 3/1992 | McQueeny |
| 5,096,822 A | 3/1992 | Rosenkrans, Jr. et al. |
| 5,097,898 A | 3/1992 | Verkaart |
| 5,103,817 A | 4/1992 | Reisdorf et al. |
| 5,106,373 A | 4/1992 | Augustine et al. |
| 5,108,372 A | 4/1992 | Swenson |
| 5,125,069 A | 6/1992 | O'Boyle |
| 5,125,900 A | 6/1992 | Teves |
| 5,129,033 A | 7/1992 | Ferrara et al. |
| 5,152,755 A | 10/1992 | Yoshinori |
| 5,153,827 A | 10/1992 | Coutré et al. |
| 5,169,389 A | 12/1992 | Kriesel |
| 5,180,896 A | 1/1993 | Gibby et al. |
| 5,183,994 A | 2/1993 | Bowles, Sr. et al. |
| 5,184,613 A | 2/1993 | Mintz |
| 5,186,057 A | 2/1993 | Everhart |
| 5,195,976 A | 3/1993 | Swenson |
| 5,205,820 A | 4/1993 | Kriesel |
| 5,211,631 A | 5/1993 | Sheaff |
| 5,217,064 A | 6/1993 | Kellow et al. |
| 5,232,439 A | 8/1993 | Campbell et al. |
| 5,241,951 A | 9/1993 | Mason et al. |
| 5,243,172 A | 9/1993 | Hazan et al. |
| 5,243,833 A | 9/1993 | Coelho et al. |
| 5,245,693 A | 9/1993 | Ford et al. |
| 5,250,032 A | 10/1993 | Carter, Jr. et al. |
| 5,254,094 A | 10/1993 | Starkey et al. |
| 5,261,411 A | 11/1993 | Hughes |
| 5,261,875 A | 11/1993 | Spears et al. |
| 5,263,323 A | 11/1993 | Maus et al. |
| 5,263,929 A | 11/1993 | Falcone et al. |
| 5,269,749 A | 12/1993 | Koturov |
| 5,276,310 A | 1/1994 | Schmidt et al. |
| 5,279,558 A | 1/1994 | Kriesel |
| 5,279,598 A | 1/1994 | Sheaff |
| 5,282,264 A | 1/1994 | Reeves et al. |
| 5,282,683 A | 2/1994 | Brett |
| 5,290,222 A | 3/1994 | Feng et al. |
| 5,290,230 A | 3/1994 | Ainsworth et al. |
| 5,296,684 A | 3/1994 | Essig et al. |
| 5,297,234 A | 3/1994 | Harms et al. |
| 5,308,335 A | 5/1994 | Ross et al. |
| 5,315,830 A | 5/1994 | Doke et al. |
| 5,318,540 A | 6/1994 | Athayde et al. |
| 5,330,431 A | 7/1994 | Herskowitz et al. |
| 5,333,326 A | 8/1994 | Faries, Jr. et al. |
| 5,338,157 A | 8/1994 | Blomquist |
| 5,342,313 A | 8/1994 | Campbell et al. |
| 5,345,923 A | 9/1994 | Luebke et al. |
| 5,348,539 A | 9/1994 | Herskowitz |
| 5,364,371 A | 11/1994 | Kamen |
| 5,364,385 A | 11/1994 | Harms et al. |
| 5,370,674 A | 12/1994 | Farrell |
| 5,381,510 A | 1/1995 | Ford et al. |
| 5,389,078 A | 2/1995 | Zalesky et al. |
| 5,392,025 A | 2/1995 | Figh et al. |
| 5,397,875 A | 3/1995 | Bechtold, Jr. |
| 5,399,007 A | 3/1995 | Marconet |
| 5,399,166 A | 3/1995 | Laing |
| 5,408,576 A | 4/1995 | Bishop |
| 5,408,577 A | 4/1995 | Weber, Jr. et al. |
| 5,411,480 A | 5/1995 | Kriesel |
| 5,411,482 A | 5/1995 | Campbell |
| 5,415,282 A | 5/1995 | Kienholz |
| 5,417,274 A | 5/1995 | Verkaart |
| 5,420,962 A | 5/1995 | Bakke |
| 5,423,759 A | 6/1995 | Campbell |
| 5,424,512 A | 6/1995 | Turetta et al. |
| 5,433,704 A | 7/1995 | Ross et al. |
| 5,451,209 A | 9/1995 | Ainsworth et al. |
| 5,474,538 A | 12/1995 | Stihler et al. |
| 5,482,373 A | 1/1996 | Hutchinson |
| 5,483,799 A | 1/1996 | Dallo |
| 5,485,408 A | 1/1996 | Blomquist |
| 5,492,534 A | 2/1996 | Athayde et al. |
| 5,494,196 A | 2/1996 | Tyner |
| 5,512,043 A | 4/1996 | Verkaart |
| 5,514,095 A | 5/1996 | Brightbill et al. |
| 5,523,055 A | 6/1996 | Hansen et al. |
| 5,531,697 A | 7/1996 | Olsen et al. |
| 5,531,698 A | 7/1996 | Olsen |
| 5,538,399 A | 7/1996 | Johnson |
| 5,540,561 A | 7/1996 | Johnson |
| 5,564,915 A | 10/1996 | Johnson |
| 5,567,119 A | 10/1996 | Johnson |
| 5,567,136 A | 10/1996 | Johnson |
| 5,572,873 A | 11/1996 | Lavigne et al. |
| 5,575,563 A | 11/1996 | Chiu et al. |
| 5,584,811 A | 12/1996 | Ross et al. |
| 5,590,648 A | 1/1997 | Mitchell et al. |
| 5,609,784 A | 3/1997 | Davenport |
| RE35,501 E | 5/1997 | Ross et al. |
| 5,634,426 A | 6/1997 | Tomlinson et al. |
| 5,647,854 A | 7/1997 | Olsen et al. |
| 5,649,910 A | 7/1997 | Kriesel et al. |
| 5,653,905 A | 8/1997 | McKinney |
| 5,658,250 A | 8/1997 | Blomquist et al. |
| 5,658,252 A | 8/1997 | Johnson |
| 5,658,478 A | 8/1997 | Roeschel et al. |
| 5,661,978 A | 9/1997 | Holmes et al. |
| 5,669,877 A | 9/1997 | Blomquist |
| 5,678,925 A | 10/1997 | Garmaise et al. |
| 5,681,284 A | 10/1997 | Herskowitz |
| 5,683,381 A | 11/1997 | Carr et al. |
| 5,690,614 A | 11/1997 | Carr et al. |
| 5,695,473 A | 12/1997 | Olsen |

(56) References Cited

U.S. PATENT DOCUMENTS

| | | | |
|---|---|---|---|
| 5,707,151 | A | 1/1998 | Parker et al. |
| 5,707,431 | A | 1/1998 | Verkaart et al. |
| 5,713,864 | A | 2/1998 | Verkaart |
| 5,720,728 | A | 2/1998 | Ford |
| 5,729,653 | A | 3/1998 | Magliochetti et al. |
| 5,733,263 | A * | 3/1998 | Wheatman .................. 604/141 |
| 5,738,442 | A | 4/1998 | Paron et al. |
| 5,743,878 | A | 4/1998 | Ross et al. |
| 5,744,806 | A | 4/1998 | Frojd |
| 5,755,275 | A | 5/1998 | Rose et al. |
| 5,772,409 | A | 6/1998 | Johnson |
| 5,779,364 | A | 7/1998 | Cannelongo et al. |
| 5,786,568 | A | 7/1998 | McKinney |
| 5,788,669 | A | 8/1998 | Peterson |
| 5,788,671 | A | 8/1998 | Johnson |
| 5,805,455 | A | 9/1998 | Lipps |
| 5,806,528 | A | 9/1998 | Magliochetti |
| 5,810,771 | A | 9/1998 | Blomquist |
| 5,816,797 | A | 10/1998 | Shoenfeld |
| 5,817,146 | A | 10/1998 | Augustine |
| 5,823,746 | A | 10/1998 | Johnson |
| 5,824,000 | A | 10/1998 | Pavlo et al. |
| 5,840,068 | A | 11/1998 | Cartledge |
| 5,858,303 | A | 1/1999 | Schiffmann et al. |
| 5,862,672 | A | 1/1999 | Faries, Jr. et al. |
| 5,875,282 | A | 2/1999 | Jordan |
| 5,876,370 | A | 3/1999 | Blomquist |
| 5,879,143 | A | 3/1999 | Cote et al. |
| 5,879,329 | A | 3/1999 | Ginsburg |
| 5,891,096 | A | 4/1999 | Hyun et al. |
| 5,893,843 | A | 4/1999 | Rodrigues |
| 5,897,207 | A | 4/1999 | Hartmann |
| 5,910,210 | A | 6/1999 | Violj et al. |
| 5,919,218 | A | 7/1999 | Carr |
| 5,924,289 | A | 7/1999 | Bishop, II |
| 5,928,196 | A | 7/1999 | Johnson et al. |
| 5,935,099 | A | 8/1999 | Peterson et al. |
| 5,935,106 | A | 8/1999 | Olsen |
| 5,954,485 | A | 9/1999 | Johnson et al. |
| 5,954,700 | A | 9/1999 | Kovelman |
| 5,961,492 | A | 10/1999 | Kriesel et al. |
| 5,961,700 | A | 10/1999 | Oliver |
| 5,961,866 | A | 10/1999 | Hansen |
| 5,977,520 | A | 11/1999 | Madison, Jr. et al. |
| 5,986,239 | A | 11/1999 | Corrigan, III et al. |
| 5,989,238 | A * | 11/1999 | Ginsburg .................. 604/500 |
| 5,997,927 | A | 12/1999 | Gics |
| 6,024,539 | A | 2/2000 | Blomquist |
| 6,035,102 | A | 3/2000 | Bakke |
| 6,039,926 | A | 3/2000 | Goldman |
| 6,045,648 | A | 4/2000 | Palmgren et al. |
| 6,062,429 | A | 5/2000 | West et al. |
| 6,096,007 | A | 8/2000 | Haan et al. |
| 6,117,122 | A | 9/2000 | Din et al. |
| 6,123,827 | A | 9/2000 | Wong et al. |
| 6,124,572 | A | 9/2000 | Spilger et al. |
| 6,129,702 | A | 10/2000 | Woias et al. |
| 6,139,528 | A | 10/2000 | Kistner et al. |
| 6,142,974 | A | 11/2000 | Kistner et al. |
| 6,146,359 | A | 11/2000 | Carr et al. |
| 6,158,458 | A | 12/2000 | Ryan |
| 6,164,469 | A | 12/2000 | Sartore |
| 6,174,300 | B1 | 1/2001 | Kriesel et al. |
| 6,175,099 | B1 | 1/2001 | Shei et al. |
| 6,175,688 | B1 | 1/2001 | Cassidy et al. |
| 6,221,045 | B1 | 4/2001 | Duchon et al. |
| 6,221,051 | B1 | 4/2001 | Hjertmon et al. |
| 6,248,077 | B1 | 6/2001 | Elson et al. |
| 6,254,572 | B1 | 7/2001 | Knipfer et al. |
| 6,257,759 | B1 | 7/2001 | Witonsky et al. |
| 6,259,067 | B1 | 7/2001 | Faries, Jr. et al. |
| 6,261,261 | B1 | 7/2001 | Gordon |
| 6,264,049 | B1 | 7/2001 | Shteynberg |
| 6,294,762 | B1 | 9/2001 | Faries, Jr. et al. |
| 6,315,767 | B1 | 11/2001 | Dumont et al. |
| 6,316,750 | B1 | 11/2001 | Levin |
| 6,334,707 | B1 | 1/2002 | Ku |
| 6,371,121 | B1 | 4/2002 | Faries, Jr. et al. |
| 6,376,805 | B2 | 4/2002 | Faries, Jr. et al. |
| 6,384,380 | B1 | 5/2002 | Faries, Jr. et al. |
| 6,464,666 | B1 | 10/2002 | Augustine et al. |
| 6,467,953 | B1 * | 10/2002 | Faries et al. .................. 374/162 |
| 6,524,239 | B1 | 2/2003 | Reed et al. |
| 6,553,336 | B1 | 4/2003 | Johnson et al. |
| 6,566,631 | B2 | 5/2003 | Faries, Jr. et al. |
| 6,607,027 | B2 | 8/2003 | Bosch et al. |
| 6,641,556 | B1 | 11/2003 | Shigezawa |
| 6,641,602 | B2 | 11/2003 | Balding |
| 6,649,040 | B1 | 11/2003 | Mirchi et al. |
| 6,660,974 | B2 | 12/2003 | Faries, Jr. et al. |
| 6,722,782 | B2 | 4/2004 | Faries, Jr. et al. |
| 6,736,788 | B1 | 5/2004 | Mongomery et al. |
| 6,740,059 | B2 | 5/2004 | Flaherty |
| 6,748,164 | B1 | 6/2004 | Kuzyk |
| 6,768,085 | B2 | 7/2004 | Faries, Jr. et al. |
| 6,788,885 | B2 | 9/2004 | Mitsunaga |
| 6,788,997 | B1 | 9/2004 | Frederick |
| 6,824,528 | B1 * | 11/2004 | Faries et al. .................. 604/113 |
| 6,850,252 | B1 | 2/2005 | Hoffberg |
| 6,860,271 | B2 | 3/2005 | Faries, Jr. et al. |
| 6,869,538 | B2 | 3/2005 | Yu et al. |
| 6,967,575 | B1 | 11/2005 | Dohrmann et al. |
| 7,031,602 | B2 | 4/2006 | Faries, Jr. et al. |
| 7,031,778 | B2 | 4/2006 | Hsiung et al. |
| 7,041,941 | B2 | 5/2006 | Faries, Jr. et al. |
| 7,090,658 | B2 | 8/2006 | Faries, Jr. et al. |
| 7,176,030 | B2 | 2/2007 | Faries, Jr. et al. |
| 7,238,171 | B2 | 7/2007 | Faries, Jr. et al. |
| 7,262,698 | B1 | 8/2007 | Frederick et al. |
| 7,276,675 | B2 | 10/2007 | Faries, Jr. et al. |
| 7,307,245 | B2 | 12/2007 | Faries, Jr. et al. |
| 7,326,882 | B2 | 2/2008 | Faries, Jr. et al. |
| 7,417,205 | B2 | 8/2008 | Faries, Jr. et al. |
| 7,540,864 | B2 | 6/2009 | Faries, Jr. et al. |
| 7,608,460 | B2 | 10/2009 | Reed et al. |
| 7,611,504 | B1 | 11/2009 | Faries, Jr. et al. |
| 7,726,876 | B2 | 6/2010 | Laverdiere et al. |
| 7,740,611 | B2 | 6/2010 | Faries, Jr. et al. |
| 7,942,851 | B2 | 5/2011 | Faries, Jr. et al. |
| 8,226,293 | B2 | 7/2012 | Faries, Jr. et al. |
| 8,226,605 | B2 | 7/2012 | Faries, Jr. et al. |
| 8,313,462 | B2 | 11/2012 | Faries, Jr. et al. |
| 8,444,599 | B2 | 5/2013 | Faries, Jr. et al. |
| 8,487,738 | B2 | 7/2013 | Faries, Jr. et al. |
| 8,636,691 | B2 | 1/2014 | Faries, Jr. et al. |
| 8,734,404 | B2 | 5/2014 | Faries, Jr. et al. |
| 8,734,405 | B2 | 5/2014 | Faries, Jr. et al. |
| 8,821,011 | B2 | 9/2014 | Faries, Jr. et al. |
| 8,845,586 | B2 | 9/2014 | Faries, Jr. et al. |
| 8,920,372 | B2 | 12/2014 | Faries, Jr. et al. |
| 8,920,387 | B2 | 12/2014 | Faries, Jr. et al. |
| 2001/0009610 | A1 | 7/2001 | Augustine et al. |
| 2002/0041621 | A1 | 4/2002 | Faries, Jr. et al. |
| 2002/0081109 | A1 | 6/2002 | Mitsunaga et al. |
| 2002/0151854 | A1 | 10/2002 | Duchon et al. |
| 2002/0156451 | A1 | 10/2002 | Lenker |
| 2002/0158058 | A1 | 10/2002 | Faries, Jr. et al. |
| 2002/0184906 | A1 | 12/2002 | Faries, Jr. et al. |
| 2003/0000939 | A1 | 1/2003 | Faries, Jr. et al. |
| 2003/0004470 | A1 | 1/2003 | Hickerson et al. |
| 2003/0114795 | A1 | 6/2003 | Faries, Jr. et al. |
| 2003/0135388 | A1 | 7/2003 | Martucci et al. |
| 2003/0216831 | A1 | 11/2003 | Hart et al. |
| 2003/0218003 | A1 | 11/2003 | Ellis et al. |
| 2003/0222933 | A1 | 12/2003 | Choi |
| 2004/0170409 | A1 | 9/2004 | Faries, Jr. et al. |
| 2004/0189258 | A1 | 9/2004 | Lehmann et al. |
| 2004/0247016 | A1 | 12/2004 | Faries, Jr. et al. |
| 2005/0059952 | A1 | 3/2005 | Giuliano et al. |
| 2005/0070845 | A1 | 3/2005 | Faries, Jr. et al. |
| 2005/0142013 | A1 | 6/2005 | Faries, Jr. et al. |
| 2005/0222933 | A1 | 10/2005 | Wesby |
| 2005/0242930 | A1 | 11/2005 | Nicolson et al. |
| 2006/0020255 | A1 | 1/2006 | Cassidy et al. |

(56) References Cited

U.S. PATENT DOCUMENTS

| | | |
|---|---|---|
| 2006/0100578 A1 | 5/2006 | Lieberman |
| 2006/0253075 A1 | 11/2006 | Faries, Jr. et al. |
| 2007/0000910 A1 | 1/2007 | Faries, Jr. et al. |
| 2007/0106243 A1 | 5/2007 | Faries, Jr. et al. |
| 2007/0142773 A1 | 6/2007 | Rosiello et al. |
| 2007/0161952 A1 | 7/2007 | Faries, Jr. et al. |
| 2007/0215018 A1 | 9/2007 | Faries, Jr. et al. |
| 2008/0021392 A1 | 1/2008 | Lurvey et al. |
| 2008/0058697 A1 | 3/2008 | Kamen et al. |
| 2008/0147016 A1 | 6/2008 | Faries et al. |
| 2008/0205481 A1 | 8/2008 | Faries et al. |
| 2010/0059498 A1 | 3/2010 | Hansen et al. |
| 2010/0082459 A1 | 4/2010 | Tusa et al. |
| 2010/0111135 A1 | 5/2010 | Faries, Jr. et al. |
| 2010/0168671 A1 | 7/2010 | Faries, Jr. et al. |
| 2010/0222762 A1 | 9/2010 | Faries, Jr. et al. |
| 2010/0222763 A1 | 9/2010 | Faries et al. |
| 2011/0297831 A1 | 12/2011 | Yao et al. |
| 2011/0307274 A1 | 12/2011 | Thompson et al. |
| 2012/0053518 A1 | 3/2012 | Faries, Jr. et al. |
| 2012/0191050 A1 | 7/2012 | Faries, Jr. et al. |
| 2012/0265336 A1 | 10/2012 | Mallet et al. |
| 2012/0285236 A1 | 11/2012 | Haartsen et al. |
| 2013/0197437 A1 | 8/2013 | Faries et al. |
| 2014/0231406 A1 | 8/2014 | Tsang et al. |
| 2014/0236615 A1 | 8/2014 | Ragusky et al. |
| 2013/0253952 A1 | 9/2014 | Burke et al. |

FOREIGN PATENT DOCUMENTS

| | | |
|---|---|---|
| DE | 197 52 578 | 6/1999 |
| EP | 0927552 A1 | 7/1999 |
| GB | 2029677 A | 3/1980 |
| GB | 2274514 | 7/1994 |
| GB | 2274514 A | 7/1994 |
| JP | 58-030666 | 2/1983 |
| JP | 7-509630 | 10/1995 |
| JP | 2000-300666 | 10/2000 |
| NZ | 331678 A1 | 3/2000 |
| WO | 9221272 | 12/1992 |
| WO | WO 98/38953 A1 | 9/1998 |
| WO | 9845658 | 10/1998 |
| WO | WO 98/45658 | 10/1998 |
| WO | 99/22786 A1 | 5/1999 |
| WO | 99/58177 A1 | 11/1999 |

OTHER PUBLICATIONS

CBI Healthcare Systems, Inc., Controlled Termperature Cabinet System, JEMS, Mar. 1997.
Koolatron, P-34 PC-3 Precision Control Thermoelectric Cooler/Warmer, Jan. 1998.
Koolatron, Canadian company announces the release of a precision control unit, Aug. 1997.
Anton, 500 miles from nowhere, it'll give you a cold drink or a warm burger . . . , Technology Update, 1993.
Koolatron, 1997 U.S. $ Price List, 1997.
Kellow et al, Drug Adulteration in Prehospital Emergency Medical Services, Oct. 1994.
CBI Medical, Inc., IV Fluid Warmer Model 8362, 1992.
Health Devices, vol. 25, No. 10, Oct. 1996.
Minco Products, Inc., Bulletin CT198, 1996.
Eurotherm Controls, Inc., Model 2116 Temperature Controller, 1997.
Ellenwood, Drop Detector, IBM Technical Bulletin, vol. 12, No. 5, Oct. 1969.
PCT International Search Report and Written Opinion, PCT/US2014/016869, Jun. 27, 2014, 10 pages.
PCT International Search Report and Written Opinion, PCT/US2014/015944, Jun. 2, 2014, 11 pages.
Cbi Healthcare Systems, Inc. Controlled Temperature Cabinet Syste, JEMS, Mar. 17, 1997.

* cited by examiner

METHOD AND APPARATUS FOR CONTROLLING PRESSURIZED INFUSION AND TEMPERATURE OF INFUSED LIQUIDS

CROSS-REFERENCE TO RELATED APPLICATIONS

This application is a divisional of U.S. patent application Ser. No. 10/095,100, entitled "Method and Apparatus for Controlling Pressurized Infusion and Temperature of Infused Liquids", and filed Mar. 12, 2002 now U.S. Pat. No. 7,238,171, which claims priority from U.S. Provisional Patent Application Ser. No. 60/275,256, entitled "Method and Apparatus for Controlled Pressure Infusion and Temperature of Infused Liquids" and filed Mar. 12, 2001. The disclosures of the above-mentioned patent applications are incorporated herein by reference in their entireties.

BACKGROUND OF THE INVENTION

1. Technical Field

The present invention pertains to pressurized infusion and temperature control systems for infused liquids, such as the type disclosed in U.S. patent application Ser. No. 09/380,507, entitled "Method and Apparatus for Pressure Infusion and Temperature Control of Infused Liquids" and filed Apr. 24, 2000, the disclosure of which is incorporated herein by reference in its entirety. In particular, the present invention is directed toward a system that controls the flow rate and temperature of a fluid within a flexible bag or container during infusion of the fluid from the container to a patient.

2. Discussion of Related Art

Intravenous (IV) fluids are typically infused into a patient utilizing a flexible bag or container filled with IV fluid and a fluid line to convey the IV fluid from the bag to the patient. The fluids are generally delivered from the container to the patient via gravitational forces and/or applied pressure. Typically, applied pressure is employed to control the infusion rate of fluid from the bag to the patient.

The related art provides several devices for regulating pressure applied to an IV fluid bag to control the infusion rate of fluid from the bag to a patient. For example, U.S. Pat. No. 4,090,514 (Hinck et al.) discloses a pressure infusion device including a bladder as part of the cuff in which a fluid filled plastic bag is encased. The bladder surrounds at least eighty percent of the plastic bag, and, upon fluid being pumped into the bladder, the fluid in the plastic bag is infused under pressure to a patient.

U.S. Pat. No. 4,551,136 (Mandl) discloses a pressure infusor for introduction of fluids into the human body. Two sheets of polyurethane overlie each other and are continuously sealed to form an air inflatable bladder. A strip of polyurethane projects from one vertical margin of the bladder to wrap completely around the liquid filled bag. A narrow elongated strap essentially attached to one margin of the infusor is long enough to wrap completely about the infusor with the bag enclosed. Velcro strips are secured to the strap to enable the strap to be fastened upon itself.

U.S. Pat. Nos. 5,308,335, 5,433,704, 5,584,811, 5,743,878 and Re. 35,501 (Ross et al.) disclose an infusion pump for infusion of a medical treatment fluid intravenously into a patient. The pump includes a collapsible treatment fluid bag juxtaposed with an inflatable drive fluid bladder confined between a pair of opposing containment members which cause the bladder to impinge against the bag as the bladder is inflated. A drive fluid pump controllably inflates the bladder, thereby displacing treatment fluid from the bag into an outlet tube affixed thereto which conveys the treatment fluid to the patient where it is received intravenously. The treatment fluid flow rate through the tube is controlled by increasing or decreasing the drive fluid pump output and consequently the pressure in the bladder in response to a pressure sensor in fluid communication with the bladder. In one embodiment, a first containment member is a rigid platen, while a second containment member is a flexible, yet inelastic, sheet loosely attached to the platen at opposite sides to form a sling. The bladder is positioned within the sling, while a fluid bag is slid into the sling in abutment with the bladder.

U.S. Pat. No. 5,681,284 (Herskowitz) discloses an infusion pump for infusion of solutions from IV bags through tubing to patients. The pump includes a housing having a compartment which receives an IV bag in a solution-dispensing position. The bag is placed over a bladder within the compartment, and the bladder is expanded by a pressurized fluid to apply a force against the bag to collapse the bag and infuse solution through the tubing. A pump in the housing pumps a fluid into the bladder in accordance with a control circuit. A pressure sensor indirectly senses pressure of fluid in the bladder through a pressure pad that contacts the bladder wall. The control circuit generates a pressure signal responsive to movement of the pressure pad for operating a valve which directs fluid between the pump and bladder.

The related art devices described above suffer from several disadvantages. In particular, the devices do not provide any control mechanism for maintaining the temperature of fluid flowing from the IV bag within a particular temperature range. This is of vital importance during infusion procedures in order to eliminate any potential for thermal shock and injury to the patient when the fluid enters the patient's body. In addition, the manual pressurization feature of the Hinck et al. and Mandl devices generally requires constant monitoring and manipulation of the devices by an operator in order to continuously maintain a desired fluid flow rate during infusion.

The related art has attempted to overcome the aforementioned problems by providing systems employing controlled pressure in combination with temperature control of IV fluid. For example, U.S. Pat. No. 5,125,900 (Teves) discloses a device for heating and pressurizing fluid filled containers. The device wraps around a flexible bag containing fluid to warm the fluid and to pressurize the bag so that warm fluid flows from the bag at a rate dependent upon the amount of pressure applied to the bag. The device includes a heating element that may be set at a preselected temperature and an inflatable bladder that may be inflated to a preselected pressure. The bladder is inflated manually utilizing a bulb.

U.S. Pat. No. 4,430,078 (Sprague) discloses a portable blood infusion pump designed to be employed in combination with a blood bag. The blood bag is located within a storage chamber that includes an inflatable bladder. Pressurized fluid is conducted within the inflatable bladder to press against the blood bag to enable discharge of the blood from the blood bag through a discharge conduit assembly. A container containing a supply of the pressurized fluid is mounted within the pump housing and is connected to the inflatable bladder. A pressure regulator is disposed in the housing to permit variance of pressure applied by the bladder against the blood bag in response to user manipulation of a knob. The pressure level applied by the bladder to the blood bag may be preset by a user via the knob while the regulator maintains the pressure level and automatically provides additional gas to the bladder in response to decreasing quantities of blood within the blood bag. An electrical heater apparatus may be included within the device to provide heat energy to the blood bag so as to warm the blood prior to being infused into a patient.

U.S. Pat. Nos. 5,879,329 and 5,989,238 (Ginsburg) disclose a system for infusing a fluid into a patient. The system includes a fluid reservoir and a temperature altering device in close proximity thereto. The temperature altering device is employed to heat or cool the fluid to a desired temperature. A positive pressure device in the form of a bladder and pressure source may be provided to place the reservoir under positive pressure while at the desired temperature. The pressure source may be connected to a processor to control the total rate and volume of fluid introduced into the bladder, thereby controlling the rate and volume of fluid leaving the reservoir. A transfer member is further provided to transfer at least some of the fluid into the patient while at the desired temperature. In addition, the system may be portable for utilization in field applications.

U.S. Pat. No. 5,733,263 (Wheatman) discloses an apparatus for heating fluid contained in one or more bags and delivering the fluid from at least one bag to a surgical patient. The apparatus includes a housing to enclose at least one bag containing fluid and having a door positioned to provide access to the housing interior. The apparatus further includes an inflatable bladder mounted in the housing interior and connected to a source of pressurized fluid for inflation. The inflatable bladder exerts force against at least one bag mounted within the housing. A regulator permits regulation of gas pressure to the bladder in response to user manipulation of a housing regulator knob. In addition, the apparatus includes a heater mounted adjacent the housing door in heat transfer relationship with the fluid and at least one bag.

The related art devices described above providing both pressurized infusion and IV fluid temperature control suffer from several disadvantages. In particular, the Teves device requires constant monitoring and manipulation by an operator to maintain a desired flow rate of IV fluid from a bag to a patient. Further, the Teves device does not completely enclose a fluid bag within the device, thereby enabling skewed or non-uniform heating of IV fluid within the bag. Similarly, the Wheatman apparatus employs a heating element assembly located on the housing door that provides heat to one surface of the IV bag. These types of heating typically produce "hot" and/or "cold" spots within the IV fluid that may cause patients to receive the fluid at inappropriate temperatures, thereby risking injury to those patients.

In addition, the Sprague, Wheatman and Ginsburg devices typically house an IV fluid bag within a housing. Thus, these devices do not permit easy access and/or viewing of the bag during infusion. This typically requires medical personnel to repeatedly access the housing interior to monitor the bag (e.g., to determine the amount of fluid remaining within the bag and whether or not the bag needs to be replaced with a new bag) and/or increases the amount of time needed to replace an existing depleted or problematic bag with a new bag. The increased time needed to replace a bag may cause serious adverse conditions for a patient, especially during critical medical situations.

OBJECTS AND SUMMARY OF THE INVENTION

Accordingly, it is an object of the present invention to control the flow rate and temperature of IV fluids being infused into a patient.

It is another object of the present invention to facilitate easy access to and visual monitoring of an IV fluid container disposed within a pressurized and temperature controlled infusion system.

Yet another object of the present invention is to uniformly heat IV fluid to a desired temperature within a pressurized and temperature controlled infusion system.

The aforesaid objects may be achieved individually and/or in combination, and it is not intended that the present invention be construed as requiring two or more of the objects to be combined unless expressly required by the claims attached hereto.

According to the present invention, a system for controlling pressurized infusion and temperature of intravenous fluids includes a housing, a heating assembly and a flexible cover. The heating assembly is recessed within the housing and includes a generally U-shaped configuration to surround and uniformly heat fluid within a fluid container placed thereon. The cover wraps around a portion of the fluid container to secure the fluid container against the heating assembly. The cover includes a pressurization member to apply a desired pressure to the fluid container to achieve a desired flow rate of intravenous fluid from the fluid container to an infusion site on a patient. The system further includes a controller to control the heating assembly and pressure within the pressurization member in accordance with desired temperature and pressure information entered into the controller for system operation.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

DETAILED DESCRIPTION OF THE PREFERRED EMBODIMENTS

Figure 1:
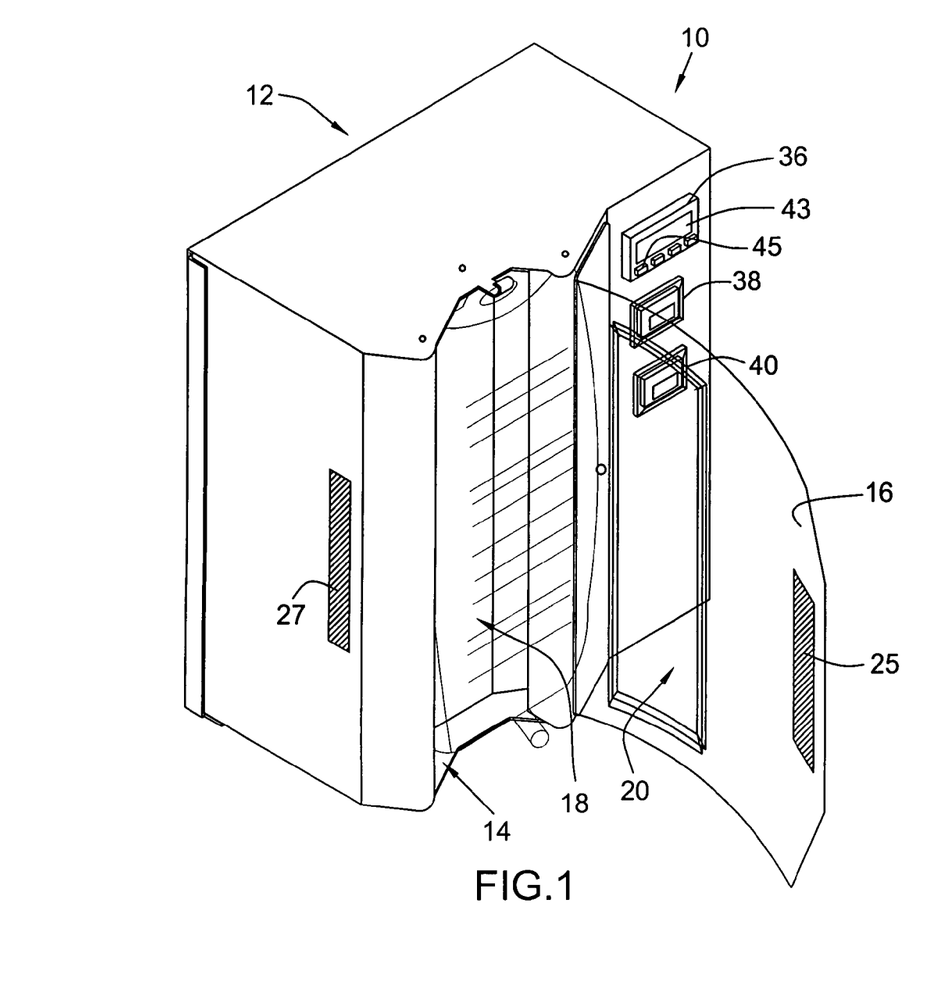
FIG. 1 is a view in perspective of a pressure and temperature controlled infusion system according to the present invention.

A pressure and temperature controlled infusion system 10 according to the present invention is illustrated in FIG. 1. Specifically, system 10 includes a housing 12, a heating plate 14 and a cover or flap 16 for securing an intravenous solution container or bag 18 to the heating plate. Cover 16 includes an inflatable bellows 20 disposed on the cover interior surface to apply pressure to the solution bag to achieve a desired solution flow or infusion rate and to force the bag against the heating plate to warm the solution. The bellows is coupled to a pump 86 (FIG. 3) that maintains a desired pressure within the bellows to achieve a particular flow or infusion rate of solution as described below. Heating plate 14 has a generally curved or arcuate configuration to permit bag 18 to conform thereto and thereby evenly distribute heat to the bag. The heating plate typically includes at least one heating pad to apply heat to the plate sections surrounding the solution bag. A controller 36 is disposed on the housing front surface to control the heating plate to heat the solution bag. The controller includes a display 43 and input devices 45 to respectively display and enter information as described below. The controller further controls pump 86 to maintain a user specified pressure within the bladder to produce a desired solution flow or infusion rate. A system power switch 38 and an inflation switch 40 are disposed on the housing below controller 36 to facilitate distribution of power to the system and control pressure to the bladder, respectively. The power and inflation switches may each include a light to illuminate that switch.

Cover 16 is constructed of a substantially transparent conformable plastic material and is generally rectangular having a side edge secured to the housing front surface. The cover is flexible and includes a conventional hook and loop fastener 25 disposed on the cover interior surface toward the cover unsecured end for engagement with a corresponding fastener 27 disposed on a housing side wall. The shorter dimension of the cover is slightly less than the longer dimension of the solution bag. The cover secures the solution bag against the housing, while the bellows applies force to the bag to achieve a desired flow rate and press the bag against the heating plate to warm solution within the bag.

Figure 2:
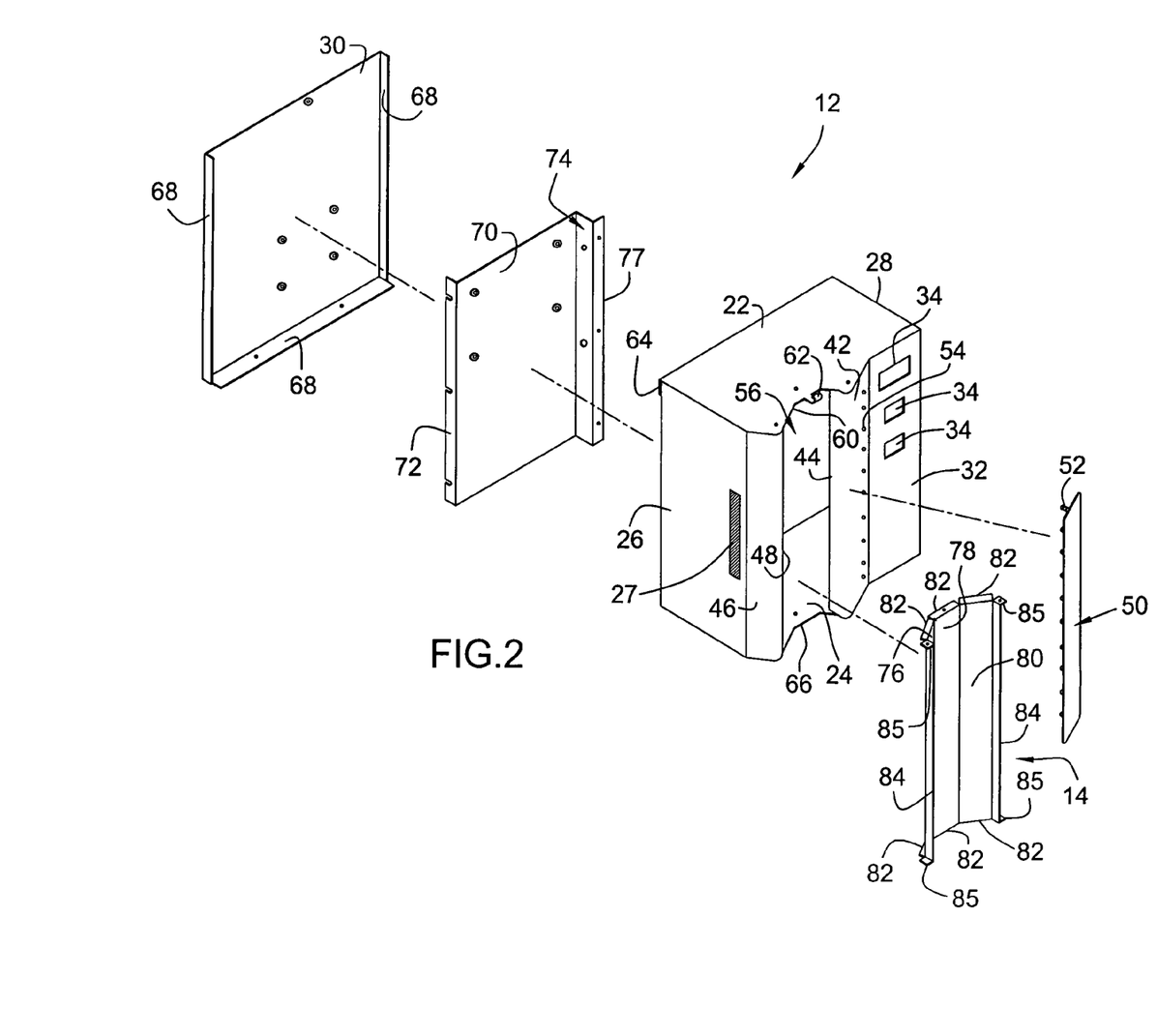
FIG. 2 is an exploded view of a housing of the system of FIG. 1.

Referring to FIG. 2, housing 12 includes top wall 22, bottom wall 24, side walls 26, 28 and a rear panel 30. Side walls 26, 28 are substantially rectangular and are attached to and extend between the housing top and bottom walls. Hook and loop fastener 27 is disposed on side wall 26 to engage cover 16 as described above. Rear Panel 30 is substantially rectangular and is attached to the top, bottom and side walls, thereby enabling the walls to collectively define the housing interior. A substantially rectangular front panel 32 is disposed between the top and bottom walls and adjoins side wall 28. The front panel includes openings 34 defined therein to receive controller 36, power switch 38 and inflation switch 40. The front panel has a height or longer dimension substantially similar to the height of the side walls, and a width or shorter dimension substantially less than rear panel 30. A substantially rectangular cover support panel 42 is disposed between the top and bottom walls and adjoins a front panel side edge. The cover support panel extends from the front panel side edge at a slight angle toward the housing exterior. The cover support panel has a longer dimension substantially similar to and a shorter dimension slightly less than the corresponding dimension of the front panel. A ledge 44 is attached to the cover support panel front edge and extends therefrom toward the housing interior. The ledge has a longer dimension substantially similar to and a shorter dimension slightly less than the corresponding dimensions of the cover support panel. A substantially rectangular cover panel 50 is attached to the cover support panel to secure an end of cover 16 to the housing. The cover panel may include bolts 52 or other devices that may be received in corresponding openings 54 defined in the cover support panel. The cover panel has dimensions similar to those of the cover support panel.

A substantially rectangular housing panel 46 is disposed between the top and bottom walls and adjoins a front edge of side wall 26. Housing panel 46 extends from side wall 26 at a slight angle toward cover support panel 42. The housing panel has dimensions similar to those of the cover support panel and includes a substantially rectangular ledge 48. The housing panel ledge is attached to the housing panel front edge and extends therefrom toward the housing interior. Ledge 48 includes dimensions similar to those of ledge 44. The housing panel and cover support panel are separated by a selected distance, thereby forming an opening or receptacle 56 therebetween. Heating plate 14 is disposed within receptacle 56 to receive and thermally treat solution bag 18 (FIG. 1).

Top wall 22 is generally rectangular and includes a truncated corner to accommodate angled housing panel 46. The top wall further includes a generally "U"-shaped recess 60 extending between the housing panel and cover support panel to accommodate the configuration of heating plate 14. The top wall further includes a hook member 62 disposed within recess 60 to engage solution bag 18, and a substantially rectangular projection 64 extending down from the top wall rear edge a slight distance to facilitate engagement with rear panel 30. Bottom wall 24 is similar to top wall 22 and is generally rectangular having a truncated corner to accommodate housing panel 46. The bottom wall further includes a generally "U"-shaped recess 66 extending between the housing panel and cover support panel to accommodate the configuration of heating plate 14.

Rear panel 30 includes substantially rectangular ledges 68 extending from the panel side and bottom edges toward the front of housing 12 to facilitate attachment of the rear panel to the housing. A substantially rectangular component panel 70 is attached to the rear panel and supports the system electrical components. The component panel includes a ledge 72 extending from a component panel side edge toward the rear panel and a projection 74 extending from the other component panel side edge toward the front of housing 12. Projection 74 is substantially rectangular and includes a substantially rectangular ledge 77 extending from the projection front edge toward housing side wall 28. Ledge 72 and projection 74 facilitate attachment of the component panel to the rear panel and housing.

Heating plate 14 includes substantially rectangular heating panels 76, 78 and 80 arranged to form a generally U-shaped heating plate configuration curved in a transverse direction (e.g., curved or arcuate along a transverse axis). The heating panels have dimensions similar to those of housing and cover support panels 42, 46 and each heating panel includes substantially rectangular ledges 82 extending from the respective heating panel top and bottom edges for a slight distance toward the housing interior. The exterior side edges of heating panels 76 and 80 each include a substantially rectangular ledge 84 extending therefrom a slight distance toward the housing exterior. Ledges 82, 84 each include substantially rectangular tabs 85 extending from the ledge top and bottom edges and facilitate attachment of the heating plate to the housing within receptacle 56. Heating plate 14 may include a heating pad 92 (FIG. 3) disposed on the underside of any of the heating panels. The heating plate configuration surrounds and evenly distributes heat to solution bag 18. The heating plate further includes a temperature sensor 90 (FIG. 3) disposed on the underside of any of the heating panels to measure and provide an indication of the heating plate temperature to the controller. The controller controls application of heat to the heating plate in accordance with the measured temperature as described below.

The system receives solution bag 18 (FIG. 1) within heating plate 14, while cover 16 extends over the solution bag to enable cover fastener 25 to engage fastener 27 on the housing side wall. Controller 36 facilitates entry of a desired pressure for bellows 20, and actuates pump 86 (FIG. 3) to supply fluid to the bellows in response to a pressure measurement being below a desired pressure. The bellows pressure is typically monitored by a pressure transducer 88 (FIG. 3) that provides the measured pressure to controller 36. The controller further controls pump and inflation solenoids 94, 96 (FIG. 3) to permit fluid to flow into and out of the bellows in accordance with the measured pressure. Similarly, the controller controls heating pad 92 in response to the heating plate temperature measured by temperature sensor 90. In particular, the system employs a heater controller 98 (FIG. 3) that is typically set to maintain the heating plate at a predetermined temperature. Controller 36 controls power to the heater controller in response to the heating plate temperature to maintain the heating plate at a desired temperature and/or to disable the heating plate in response to excessive heating plate temperatures as described below.

Figure 3:
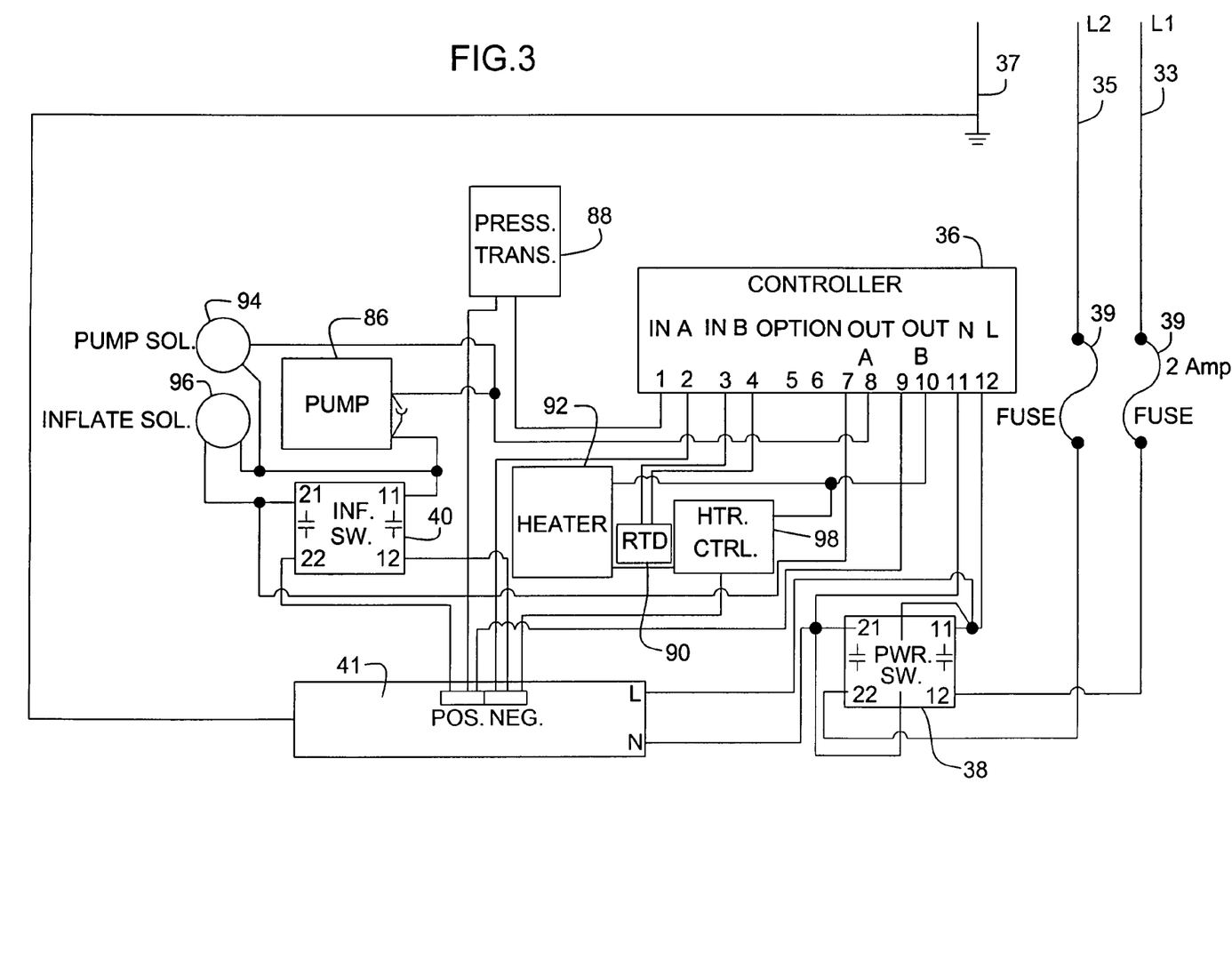
FIG. 3 is an electrical schematic diagram of an exemplary control circuit for the system of FIG. 1.

An exemplary control circuit for controlling system operation is illustrated in FIG. 3. Specifically, lines 33, 35 and 37 represent power received from a system power cord (not shown) with line 37 connected to ground. Lines 33, 35 are each connected in series with a corresponding fuse 39, preferably a two amp fuse, to protect the circuit from power surges and spikes. Lines 33, 35 are connected to power switch 38 that controls power to the circuit. The power switch enables a power supply 41 to provide power to heating pad 92 via controller 36 and heater controller 98. Controller 36 is connected to power supply 41, heater controller 98 and heating pad 92. The heater controller is typically set to provide power to heating pad 92 to maintain the heating plate at a predetermined temperature. Controller 36 controls power to the heater controller based on a temperature measurement of the heating plate. Temperature sensor 90, preferably a resistive temperature device (RTD), measures resistance through the heating plate and provides a temperature indication to controller 36. Controller 36 disables power to heater controller 98 in response to the measured temperature indicating excessive heating plate temperatures. In effect, this arrangement serves as a safety device to disable the heating plate in response to excessive temperatures.

Alternatively, heater controller 98 may be set to maintain the heating plate at a temperature above desired temperatures. A desired temperature may be entered into controller 36 wherein that controller compares the measured heating plate temperature to the desired temperature. When the measured heating plate temperature is below the desired temperature, controller 36 maintains or enables power to heater controller 98. Conversely, if the measured heating plate temperature exceeds the desired temperature, controller 36 disables power to heater controller 98. Thus, controller 36 may maintain heating plate 14 at a desired temperature by enabling or disabling power to the heater controller. The heater controller may control any quantity of heating pads, or the circuit may employ a heater controller for each heating pad to control the heating plate temperature based on signals from controller 36 as described above.

Inflation switch 40 is connected to power supply 41 and controls distribution of power to pump 86 and pump and inflation solenoids 94, 96 to facilitate automatic control of pressure within bellows 20. Controller 36 is further connected to pump 86, pump solenoid 94 and inflation solenoid 96. Pressure transducer 88 measures pressure within bellows 20 and provides a pressure indication to controller 36. Controller 36 actuates pump 86 in response to the bellows pressure being below a desired pressure. In particular, a desired pressure is entered into controller 36, wherein that controller compares the measured pressure to the desired pressure. When the measured pressure is below the desired pressure, controller 36 actuates pump 86 and inflation solenoid 96 to facilitate pumping of fluid within the bellows, thereby inflating or increasing pressure within the bellows. The pump is typically enabled until the bellows pressure is equal to or greater than the desired pressure as indicated by the pressure transducer. If the measured pressure exceeds the desired pressure, controller 36 actuates pump solenoid 94 to release fluid from the bellows, thereby decreasing the bellows pressure. The pump solenoid is typically enabled until the bellows pressure is equal to or less than the desired pressure as indicated by the pressure transducer. The inflation solenoid basically serves as a valve to maintain fluid within and enable fluid to enter the bellows, while the pump solenoid serves as a valve to release fluid and pressure from the bellows. The bellows is connected to the pump via a tube (not shown) where fluid flow within the tube is controlled by the pump and inflation solenoids as described above. The lines, fuses, power supply, switches, controllers, heating pad, solenoids, pressure and temperature sensors, pump and other circuit components may be implemented by any conventional or other components performing the above described functions. The control circuitry is typically disposed on the component panel within housing 12.

Operation of the infusion system is described with reference to FIGS. 1-3. Specifically, an intravenous solution bag is placed within heating plate 14 and typically secured therein by cover 16 and hook member 62. Power switch 38 is enabled to provide power to the system. The heater controller is typically set to maintain the heating plate at a predetermined temperature as described above, while a desired pressure may be entered by a user into controller 36. The control circuit measures the temperature of heating plate 14 and disables the heater controller as described above in response to the measured temperature attaining excessive levels. Alternatively, the heater controller may be set to maintain the heating plate temperature above desired levels, while a desired temperature may be entered into controller 36 by the user. The control circuit measures the temperature of heating plate 14 and enables or disables the heater controller in response to the measured heating plate temperature as described above to maintain the heating plate at the desired temperature. Controller 36 may display the measured heating plate temperature and/or the desired temperature entered by the user on display 43.

The temperature control of the system is generally enabled in response to actuation of power switch 38, while pressure control is typically enabled in response to actuation of the power and inflation switches. The control circuit measures the pressure within bellows 20 and controls pump 86 and solenoids 94, 96 to inflate or deflate the bellows in accordance with the measured pressure as described above. The system therefore maintains a consistent pressure on the solution bag during bag depletion to maintain a desired solution flow rate to the patient. The desired and/or measured bellows pressure may be displayed by controller 36 on display 43. The system may be mounted on any type of supporting structure (e.g., IV or other pole, wall, etc.) to provide infusion with controlled pressure and temperature to a patient.

It will be appreciated that the embodiments described above and illustrated in the drawings represent only a few of the many ways of implementing a method and apparatus for controlling pressurized infusion and temperature of infused liquids.

The housing may be of any shape or size, and may be constructed of any suitable materials. The housing walls, panels (e.g., rear panel, front panel, cover support panel, cover panel, housing panel, component panel, etc.), ledges, projections and other structural components may be of any quantity, shape or size, may be constructed of any suitable materials, and may be attached or connected via any suitable techniques (e.g., fasteners, welding, formed as integral components, etc.). The recesses within the top and bottom walls may be of any shape or size and disposed within any housing walls at any suitable locations. The hook member may be of any shape or size and may be disposed at any location on the housing. The front panel openings may be of any quantity, shape or size and disposed at any suitable locations to receive the corresponding components (e.g., switches, controllers, etc.). The receptacle for receiving the heating plate may be of any shape or size and may be disposed at any suitable location. Alternatively, the heating plate may be disposed on the housing without the receptacle. The housing may be supported on any type of support structure (e.g., IV or other pole, wall, counter, etc.) and may include any quantity of handles disposed at any locations for portability. The housing may be in the form of a box-like structure and receive the solution bag within the housing interior. The housing may be positioned in any desired orientation for system operation.

The conformable cover may be of any shape or size and may be constructed of any suitable materials. The cover is preferably constructed of transparent materials to permit clear viewing of the solution bag, but may alternatively be constructed of any translucent or opaque materials, or any combination of transparent, translucent and opaque materials. Any portion of the cover may be secured to the housing at any locations via any conventional or other fastening techniques (e.g., bolts, screws, adhesives, etc.). Further, any conventional or other fasteners (e.g., hook and loop, hooks, clasps, etc.) may be utilized to removably secure the cover to the housing. The cover may be disposed on the housing in any fashion and open from any direction (e.g., top, bottom, side, etc.) to removably secure the solution bag to the housing. Alternatively, the housing may include a roller type device to engage the cover unsecured end and wind the cover about the roller to apply pressure to and retain the solution bag. The roller device may be controlled to apply a desired amount of force to the bag, and may be utilized with or without the bellows. Moreover, the cover and/or bellows may further include a heating device (e.g., resistive wires, heating pad, etc.) to facilitate heating of the solution bag on plural sides.

The infusion system may include any combination of bellows and/or heating plates and heating pads. For example, the system may include one or more bellows capable of applying pressure to the solution bag but no heating plates or heating pads. Alternatively, the system may include any number of heating plates and heating pads to heat the solution bag to a desired temperature but no bellows. Further still, the system may include any suitable number of bellows in combination with any suitable number of heating plates and pads.

The bellows may be implemented by any inflatable device capable of expanding upon inflation, and may be inflated via any type of fluid, such as a gas (e.g., air) or liquid. The fluid may be heated in order to inflate the bellows and heat the solution bag. The bellows may be of any shape or size capable of applying pressure to the solution bag, may be constructed of any suitable materials, and may be disposed at any location and/or oriented in any fashion on the cover or within the housing. For example, the bellows may be disposed behind the heating plate and expand to force the heating plate against the solution bag to warm the solution and initiate a desired solution flow rate. The heating plate is typically hinged in this arrangement to transition between expanded and collapsed states in response to inflated and deflated states of the bellows, respectively. Further, any quantity (e.g., at least one) of bellows may be utilized to apply pressure to the solution bag in substantially the same manner described above. The hose for directing fluid to and from the bellows may be implemented by any conventional or other type of hose or tube, may be of any size or shape, and may be constructed of any suitable materials. The bellows may be inflated by any type of inflating device or pump including any type of valve or other device for controlling inflation and deflation of the bellows.

The heating plate may include any quantity of heating panels of any shape or size and constructed of any suitable materials. The heating panels may be arranged in any fashion to form any type of heating plate configuration. The heating plate may include any quantity of conventional or other heating devices (e.g., heating pads, resistive wires, etc.) of any shape or size disposed at any suitable locations on the heating plate. The temperature sensor may be implemented by any quantity of any conventional or other type of temperature measuring devices disposed at any locations on the heating plate. Alternatively, a temperature sensor may be disposed in contact with the solution bag to directly measure a solution temperature.

The control circuit may include any conventional or other types of fuses (e.g., for any suitable current limit), controllers, switches (e.g., lighted), power supplies and other components. The controllers are each typically implemented by a commercially available controller pre-programmed and loaded with its own software, but may be implemented by any quantity of any conventional or other type of controller, microprocessor, or circuitry capable of controlling the heating plate and/or pump. The system controller may be disposed at any location on the housing and include any types of displays, lights or other indicators, or switches (e.g., lighted) arranged in any fashion. The display may be disposed at any locations on the controller and/or housing and/or be remote from the system and may be implemented by any quantity of any conventional or other types of displays, such as LED or LCD displays. The system controller may be configured to directly control the heating plate in response to the measured temperature and a temperature entered by the user, and disable the heating plate in response to excessive temperatures. The power and inflation switches may be disposed on the housing at any locations and may be implemented by any quantity of any type of conventional or other type of switch or button that may include a light for illuminating the switch or button. The displays may display any quantity of digits to reflect the actual and set point pressures and/or temperatures. Further, the display may display any desired information. The system controller may include any quantity of any types of input devices (e.g., buttons, keypad, voice recognition, etc.) disposed at any locations on the housing and/or controller to facilitate entry of information and/or selective control of the display to display any desired information (e.g., desired temperature and/or pressure, actual temperature and/or pressure, etc.).

The power supply may be implemented by any quantity of conventional or other type of power supply, while the solenoids may be implemented by any quantity of any type of conventional or other solenoid or valve to control fluid flow into and out of the bellows. The pump may be implemented by any quantity of any conventional or other pumping device. The pressure transducer may be implemented by any quantity of any conventional or other pressure measuring or sensing device and may be disposed at any suitable locations to measure bellows pressure (e.g., measure pressure within the bellows and/or pump hose, measure pump pressure and/or flow, measure force applied by bellows, etc.). The pressure and temperature control features of the present invention may be utilized individually and/or in any combination in response to system power and/or actuation of any quantity of any types of switches. The system may be configured to accommodate any quantity of solution bags or other containers of any shape or size. The present invention is not limited to the applications disclosed herein, but may be utilized for infusion of any fluids (e.g., saline, blood, antibiotics or other drugs, gases, etc.).

It is to be understood that the terms "top", "bottom", "front", "rear", "side", "height", "width", "length", "upper", "lower" and the like are used herein merely to describe points of reference and do not limit the present invention to any particular configuration or orientation.

From the foregoing description, it will be appreciated that the invention makes available a novel method and apparatus for controlling pressurized infusion and temperature of infused liquids, wherein a bag or container of an IV fluid is secured to a system heating assembly via a flexible cover including a bellows to facilitate controlled pressurized infusion and temperature of the fluid during infusion from the container to a patient.

Having described preferred embodiments of a new and improved method and apparatus for controlling pressurized infusion and temperature of infused liquids, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for controlling pressurized infusion and temperature of intravenous fluids comprising:
    a housing including a housing exterior surface with a recessed portion;
    a heating assembly disposed along said recessed portion of said housing exterior surface to heat an intravenous fluid container to a desired temperature;
    a flexible cover to wrap around and conform to a portion of said fluid container to secure said fluid container against said recessed heating assembly;
    a pressurization member to apply a desired pressure to said fluid container and control a flow rate of intravenous fluid from said fluid container to a patient; and
    a controller to control at least one of said heating assembly and said pressurization member.

2. The system of claim 1, wherein said controller controls said heating assembly to heat said fluid container to the desired temperature.

3. The system of claim 2, further including:
    a temperature sensor to measure a temperature of said heating assembly, wherein said temperature sensor is coupled to said controller to facilitate control of said heating assembly to heat said fluid container to the desired temperature in accordance with said measured temperature.

4. The system of claim 3, wherein said heating assembly includes:
    a heating plate to receive said fluid container;
    a heater disposed proximate at least a portion of said heating plate to apply heat to said heating plate and said fluid container; and
    a heater controller coupled to said heater to control said heater to heat said heating plate to a predetermined temperature;
    wherein said heater controller is controlled by said controller to facilitate heating of said fluid container to the desired temperature.

5. The system of claim 1, wherein said controller controls said pressurization member to apply the desired pressure to said fluid container.

6. The system of claim 5, wherein said pressurization member includes an inflatable bellows, and said controller controls inflation and deflation of said bellows to achieve application of the desired pressure to said fluid container.

7. The system of claim 5, further including:
    a pressure sensor to measure pressure within said pressurization member, wherein said pressure sensor is coupled to said controller to facilitate control of said pressurization member in accordance with said measured pressure.

8. The system of claim 7, further including:
    a pump to inflate said pressurization member with a fluid; and
    a release valve to facilitate deflation of said pressurization member by releasing fluid therefrom;
    wherein said pump and release valve are coupled to said controller to facilitate control of said pressurization member to apply the desired pressure to said fluid container.

9. The system of claim 1, wherein said pressurization member is disposed on said cover.

10. The system of claim 1, wherein said heating assembly includes a heating plate with a generally U-shaped configuration to receive said fluid container and substantially uniformly distribute heat thereto.

11. The system of claim 1, further comprising an input device coupled to said controller to facilitate entry of control information to said controller, wherein said control information includes at least one of the desired temperature and the desired pressure.

12. A system for controlling pressurized infusion and temperature of intravenous fluids comprising:
    a housing including a housing exterior surface with a recessed portion;
    heating means disposed along said recessed portion of said housing exterior surface for heating an intravenous fluid container to a desired temperature;
    wrap means for wrapping around and conforming to a portion of said fluid container to secure said fluid container against said recessed heating means;
    pressurization means for applying a desired pressure to said fluid container and controlling a flow rate of intravenous fluid from said fluid container to a patient; and
    control means for controlling at least one of said heating means and said pressurization means.

13. The system of claim 12, wherein said pressurization means includes an inflatable bellows, and said control means controls inflation and deflation of said bellows to achieve application of the desired pressure to said fluid container.

14. The system of claim 12, wherein said pressurization means is disposed on said wrap means.

15. The system of claim 12, further including:
    pressure sensing means for measuring pressure within said pressurization means, wherein said pressure sensing means is coupled to said control means to facilitate control of said pressurization means in accordance with said measured pressure.

16. The system of claim 15, further including:
    pumping means for inflating said pressurization means with a fluid; and
    deflating means for deflating said pressurization means by releasing fluid therefrom;
    wherein said pump means and said deflating means are coupled to said control means to facilitate control of said pressurization means to apply the desired pressure to said fluid container.

17. The system of claim 12, further including:
    temperature sensing means for measuring a temperature of said heating means, wherein said temperature sensing means is coupled to said control means to facilitate control of said heating means to heat said fluid container to the desired temperature in accordance with said measured temperature.

18. The system of claim 17, wherein said heating means includes:
- a heating plate to receive said fluid container;
- a heater disposed proximate at least a portion of said heating plate to apply heat to said heating plate and said fluid container; and
- heater control means coupled to said heater to control said heater to heat said heating plate to a predetermined temperature;
- wherein said heater control means is controlled by said control means to facilitate heating of said fluid container to the desired temperature.

19. The system of claim 12, wherein said heating means includes a heating plate with a generally U-shaped configuration to receive said fluid container and substantially uniformly distribute heat thereto.

20. The system of claim 12, further comprising entry means coupled to said controller for facilitating entry of control information to said control means, wherein said control information includes at least one of the desired temperature and the desired pressure.

21. A system for controlling pressurized infusion of intravenous fluids comprising:
- a housing including a housing exterior surface;
- a receptacle recessed within said housing exterior surface to receive an intravenous fluid container;
- a flexible cover to wrap around and conform to a portion of said fluid container to secure said fluid container within said receptacle;
- a pressurization member to apply a desired pressure to said fluid container and control a flow rate of intravenous fluid from said fluid container to a patient; and
- a controller to control pressure applied by said pressurization member.

22. The system of claim 21, wherein said pressurization member is disposed on said cover.

23. The system of claim 21, further including:
- a pressure sensor to measure pressure within said pressurization member, wherein said pressure sensor is coupled to said controller to facilitate control of said pressurization member in accordance with said measured pressure.

24. A system for controlling temperature of intravenous fluids comprising:
- a housing including a housing exterior surface with a recessed portion;
- a heating assembly disposed along said recessed portion of said housing exterior surface to heat an intravenous fluid container to a desired temperature;
- a flexible cover to wrap around and conform to a portion of said fluid container to secure said fluid container against said recessed heating assembly; and
- a controller to control said heating assembly.

25. The system of claim 24, further including:
- a temperature sensor to measure a temperature of said heating assembly, wherein said temperature sensor is coupled to said controller to facilitate control of said heating assembly to heat said fluid container to the desired temperature in accordance with said measured temperature.

26. The system of claim 25, wherein said heating assembly includes:
- a heating plate to receive said fluid container;
- a heater disposed proximate at least a portion of said heating plate to apply heat to said heating plate and said fluid container; and
- a heater controller coupled to said heater to control said heater to heat said heating plate to a predetermined temperature;
- wherein said heater controller is controlled by said controller to facilitate heating of said fluid container to the desired temperature.

27. The system of claim 24, wherein said heating assembly includes a heating plate with a generally U-shaped configuration to receive said fluid container and substantially uniformly distribute heat thereto.

* * * * *